United States Patent [19]

Petrov et al.

[11] Patent Number: 5,229,525

[45] Date of Patent: Jul. 20, 1993

[54] METHOD FOR PREPARING PERFLUORO-OXAZIRIDINES

[75] Inventors: Viatcheslav A. Petrov; Darryl D. Desmarteau, both of Clemson, S.C.; Walter Navarrini, Milan, Italy

[73] Assignee: Ausimont S.p.A., Milan, Italy

[21] Appl. No.: 824,611

[22] Filed: Jan. 23, 1992

[30] Foreign Application Priority Data

Jan. 24, 1991 [IT] Italy .................. MI91A000172

[51] Int. Cl.$^5$ .................................. C07D 269/00
[52] U.S. Cl. ........................................ 548/959
[58] Field of Search ............................. 548/959

[56] References Cited

U.S. PATENT DOCUMENTS

| | | | |
|---|---|---|---|
| 4,178,292 | 12/1979 | Tellier et al. | 548/959 |
| 4,287,128 | 9/1981 | Ratcliff | 549/523 |
| 4,874,875 | 10/1989 | Navarrini et al. | 548/959 |

FOREIGN PATENT DOCUMENTS 0338585 10/1989 European Pat. Off.
0743940 1/1956 United Kingdom.

OTHER PUBLICATIONS

Falardeau et al, "Direct Synthesis of Fluorinated Peroxides", *J. Am. Chem. Soc.* 98:12, 3529–3532, (1976).
Barr and Hazeldine, J. Chem. Soc. (1955) 1881–1889.
Zheng and DesMarteau, J. Org. Chem. 48, (1983) 4844–4847.
Peterman and Shreeve, Inorg. Chem. 14, (1975) 1223–1228.
L. Bragante et al., Journal of Fluorine Chemistry 53, 181–97 (1991).
R. G. Pews, Journal of Organic Chemistry, 32, 1628 (1967).
Introduction to Organic Chemistry (2d Edition 1981), Andrew Streitwieser, Jr. et al., p. 320.

*Primary Examiner*—Joseph Paul Brust
*Assistant Examiner*—Jacqueline Haley
*Attorney, Agent, or Firm*—Bryan Cave

[57] ABSTRACT

A process for preparing perfluoro-oxyaziridines of formula:

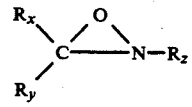

where $R_x$ is F, a $C_1$–$C_{10}$ perfluoroalkyl group or a $-NR^f{}_2$ group in which $R^f$ is a $C_1$–$C_{10}$ perfluoroalkyl group, $R_y$ is F or a $C_1$–$C_{10}$ perfluoroalkyl group and $R_z$ is a $C_1$–$C_{10}$ perfluoroalkyl group. The process consists in reacting the corresponding perfluoroimine with an aromatic peroxyacid having a benzenic nucleus, in an aprotic solvent, at a temperature ranging from $-50°$ to $+100°$ C.

8 Claims, No Drawings

METHOD FOR PREPARING PERFLUORO-OXAZIRIDINES

The present invention relates to a process for preparing perfluoro-oxyaziridines.

The simplest perfluoro-oxyaziridine is perfluoro-2-azapropane oxide:

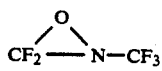

A process for preparing this compound has been described by Falardeau and DesMarteau in J. Am. Chem. Soc., 98, 3529 (1976). It comprises adding trifluoromethyl hydroperoxide $CF_3OOH$ to the corresponding imine $CF_3N=CF_2$ and subsequently converting the resulting hydroperoxide to oxyaziridine through NaF.

This process exhibits several drawbacks, which are mainly due to hydroperoxide $CF_3OOH$ used as an oxidant, which is potentially explosive and is preparable only by means of a complex multistep process.

The same process described by Falardeau and DesMarteau has been utilized by Zheng and DesMarteau (J. Org. Chem., 48, 4844 (1983)) for preparing oxyaziridines of formula:

from the corresponding imines. By means of this process, however, it is not possible to prepare oxyaziridines substituted, on the carbon atom, by perfluoroalkyl groups.

Another method for preparing perfluoro-oxyaziridines is described in U.S. Pat. No. 4,287,128, where a perhaloalkyl imine is reacted with gaseous chlorine in the presence of a carbonate or bicarbonate of an alkali or alkaline-earth metal. The presence of water traces is necessary to catalyze the reaction. This fact represents a drawback as both the starting imines and the obtained oxyaziridines hydrolize easily, in particular when they are non-substituted. By consequence, said method cannot be used for preparing perfluoro-2-azapropene oxide.

U.S. Pat. No. 4,874,875 describes another process for synthesizing perfluoro-oxyaziridines. It consists in reacting a perfluoroimine with $H_2O_2$, in the presence of a base, in an aprotic polar solvent. Owing to the presence of the water deriving from $H_2O_2$, neither this process can be utilized for preparing perfluoro-2-azapropene oxide.

Thus, for preparing said first member of the class of perfluoro-oxyaziridines, only the complicated method disclosed by Falardeau and DesMarteau is utilizable, which is affected with the above-described drawbacks.

The Applicant has now surprisingly found that the perfluoro-oxyaziridines can be prepared by reacting the corresponding perfluoro-imines with an aromatic peroxyacid in an aprotic solvent; in particular, the process is utilizable for preparing, with good yields, perfluoro-oxyaziridines non-substituted on the carbon atom, such as perfluoro-2-azapropene oxide.

Thus, an object of the present invention is a process for preparing perfluoro-oxyaziridines of formula:

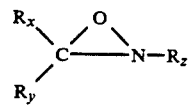

wherein:

$R_x$ is F, a perfluoroalkyl group having 1 to 10 carbon atoms or a $—NR_f 2$ group in which $R_f$ is a perfluoroalkyl group having 1 to 10 carbon atoms, $R_y$ is F or a perfluoroalkyl group having 1 to 10 carbon atoms, $R_z$ is a perfluoroalkyl group having 1 to 10 carbon atoms.

The process consists in reacting a perfluoro-imine of formula:

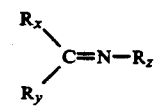

where $R_x$, $R_y$ and $R_z$ are the same as defined hereinbefore, with an aromatic peroxyacid of formula:

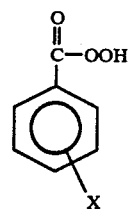

where X is H or an electron-attractor substituent, in an aprotic solvent, at a temperature ranging from $-50°$ to $+100°$ C.

The starting perfluoro-imines are known compounds and are preparable according to the methods described, for example, in "Organic Fluorine Chemistry" by W. A. Sheppard and C. M. Sharts, W. A. Benjamin Inc. (1969) and in Inorg. Chem., 14, 1223 (1975) by K. E. Peterman and J. M. Shreeve. In particular for $CF_2=N—CF_3$ it is possible to utilize the process described by Barr and Haszeldine in J. Chem. Soc., 1881 (1955).

The $R_x$, $R_y$ and $R_z$ groups have preferably from 1 to 8 carbon atoms. The $R_f$ group has preferably from 1 to 3 carbon atoms.

As regards the aromatic peroxyacids of formula (III), substituent X can be in ortho, meta or para position with respect to the peroxycarboxylic group and it is preferably selected from F, Cl, $—NO_2$, $—COOR$ and $—CONR_2$, where R is H or an alkyl group preferably having from 1 to 5 carbon atoms.

Examples of aromatic peroxyacids utilizable in the process of the present invention are: m-chloroperoxybenzoic acid, p-nitroperoxybenzoic acid, p-methoxycarboxy-peroxybenzoic acid, monoperoxyphthalic acid. Particularly preferred is m-chloroperoxybenzoic acid.

As already mentioned, the reaction is conducted in an aprotic solvent. It is possible to utilize any solvent of this type compatible with the peroxyacid and with the perfluoro-imine. Utilizable are, for example, nitriles (such as acetonitrile and benzonitrile), ethers (such as diethylether, dioxane, tetrahydrofuran, 2-methoxyethylether), chlorinated hydrocarbons (such as dichloromethane, terachloromethane, chloroform, monochloroethane) or mixtures thereof.

Acetonitrile and dichloromethane are preferred.

Preferably, the solvent and the peracid are thoroughly anhydrified prior to the reaction in order to avoid the hydrolysis of the starting amine and of the oxyaziridine. This procedure is particularly recommended when oxyaziridines non-substituted on the carbon atom, such as perfluoro-2-azapropene oxide, are to be prepared.

Conventional techniques are utilizable to this purpose. For example, the solvent can be distilled in the presence of an anhydrifying agent (for example $P_2O_5$, $CaCl_2$, $MgSO_4$, etc.), while the peroxyacid can be kept in contact with any anhydrifying agent which is compatible with the peroxyacid itself. Suitable for this purpose are, for example, the common molecular sieves.

The reaction temperature ranges from $-50°$ to $+100°$ C., preferably from $-50°$ to $+50°$ C.

The peroxyacid/imine molar ratio is generally in the range of from 1:1 to 10:1, preferably from 1:1 to 2:1.

The reaction time is not a critical parameter and is a function of the selected reaction temperature. Generally, the reaction is concluded in a time ranging from 10 minutes to 24 hours.

The perfluoro-oxyaziridines preparable by the process of the present invention are utilized for the synthesis of polymers or copolymers characterized by a high chemical inertia and by a high thermal stability, such as the perfluoroaminoether polymers described in patent application EP-338,585.

The perfluoro-oxyaziridines can be utilized also in the preparation of nitrons. Furthermore, they form complexes with the ions of transition metals, which act as catalysts for the photopolymerization of ethylene monomers.

The following examples are given for illustrative purposes and are by no way to be considered as a limitation of the scope of the present invention.

EXAMPLE 1

Preparation of

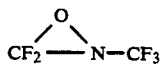

Into a Pyrex ®50 ml flask there were introduced, inside a dry-box, 2.0 g (7.0 mmols) of m-chloro-peroxybenzoic acid (MCPBA), a commercial product of Aldrich Co., containing 75-80% of MCPBA, the remaining portion being m-chloro-benzoic acid.

The MCPBA was dissolved in 25 ml of $CH_2Cl_2$ (commercial product of Aldrich), previously distilled on $P_2O_5$. The solution was maintained in contact with molecular sieves (Fisher M-564, type 3A, 8-12 mesh) for 50 minutes, at room temperature. The solution was then transferred into another 50 ml flask equipped with a magnetic stirrer.

The flask was cooled with liquid nitrogen ($-196°$ C.) and evacuated. By means of a Pyrex ® vacuum line, 0.4 g (3.0 mmols) of perfluoro-2-azapropene $CF_2=N-CF_3$ were condensed in the flask.

The flask was introduced into a water-ice bath. The reaction mixture was stirred for 15 minutes at 0° C.

Through vacuum distillation there were recovered 0.24 g (1.6 mmols) of perfluoro-2-azapropene oxide (yield: 53%).

The oxyaziridine was identified by comparing the IR and $^{19}F$-NMR spectra with the data of the literature.

EXAMPLE 2

Preparation of

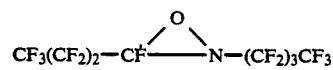

5.4 g (25.0 mmols) of MCPBA (commercial product as in example 1) were introduced, inside a dry-box, into a 50 ml flask.

The MCPBA was dissolved in 30 ml of $CH_3CN$ (commercial product manufactured by Aldrich). The solution was maintained in contact with molecular sieves for 40 minutes at room temperature. Then it was transferred into another 50 ml flask equipped with a magnetic stirrer, and it was cooled to $+10°$ C.

10.0 g (23.0 mmols) of $CF_3(CF_2)_2-CF=N-(CF_2)_3CF_3$ were added. The reaction mixture was maintained under stirring at $+10°$ C. for 5 minutes, was allowed to heat up to room temperature in 10 minutes and then was diluted with 70 ml of $CH_3CN$ so as to dissolve the precipitate which had formed during the reaction.

The product so obtained was separated by means of a separatory funnel, anhydrified on $CaCl_2$ for 1 hour and then distilled. 8.2 g (18.3 mmols) of pure oxyaziridine (yield: 79%), which was characterized through the IR, $^{19}F$-NMR and mass spectra, were recovered.

EXAMPLE 3

Preparation of

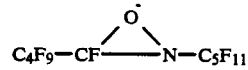

5.0 g (22.0 mmols) of MCPBA, dissolved in 25 ml of $CH_3CN$, were reacted with 8.0 g (15.0 mmols) of a 1:1 isomeric mixture of the perfluoro-imines of formula: $CF_3(CF_2)_3-CF=N-(CF_2)_4CF_3$ and $CF_3CF_2CF(CF_3)-CF=N-(CF_2)_4CF_3$.

Following the same procedure described in example 2, 6.5 g (11.8 mmols) of pure oxyaziridine (yield: 79%) were obtained. The boiling point was 68°-70° C./135 mm Hg.

On the basis of the IR and $^{19}F$-NMR spectra and of the gaschromatographic data, the obtained product resulted to consist of a 1:1 mixture of the two isomers of formula:

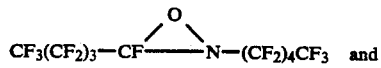

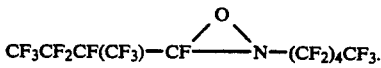

EXAMPLE 4

Preparation of

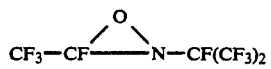

3.5 g (15.3 mmols) of MCPBA, dissolved in 25 ml of CH$_3$CN, were reacted with 3.5 g (12.4 mmols) of CF$_3$—CF=N—CF(CF$_3$)$_2$ according to the same procedure illustrated in example 2.

There were obtained 1.4 g (4.9 mmols) of pure oxyaziridine (yield: 39%).

The product was characterized through the IR, $^{19}$F-NMR and mass spectra.

EXAMPLE 5

Preparation of

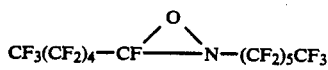
CF$_3$(CF$_2$)$_4$—CF————N—(CF$_2$)$_5$CF$_3$ 4.0 g (17.4 mmols) of MCPBA, dissolved in 25 ml of CH$_3$CN, were reacted with 6.0 g (9.5 mmols) of: CF$_3$(CF$_2$)$_4$—CF=N—(CF$_2$)$_5$CF$_3$, following the same procedure as is described in example 2.

4.3 g (6.6 mmols) of pure oxyaziridine were obtained (yield: 70%).

The product was identified through the IR and $^{19}$F-NMR spectra.

EXAMPLE 6

Preparation of

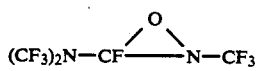
(CF$_3$)$_2$N—CF————N—CF$_3$ 1.0 g (4.4 mmols) of MCPBA was dissolved in 10 ml of CH$_3$CN and maintained in contact with molecular sieves for 45 minutes, at room temperature. The solution was transferred into a 50 ml flask equipped with a magnetic stirrer. The flask was cooled with liquid nitrogen (−196° C.) and then it was evacuated.

Into the flask there were condensed, by means of a Pyrex® vacuum line, 0.8 g (3.0 mmols) of (CF$_3$)$_2$N—CF=N—CF$_3$. The reaction mixture was heated to room temperature in 10 minutes, then it was stirred for 15 minutes at that temperature. Through vacuum distillation there were obtained 0.5 g (1.82 mmols) of pure oxyaziridine (yield: 61%).

The product was identified by comparing the IR and $^{19}$F-NMR spectra with the data of the literature.

We claim:

1. A process for preparing perfluorooxyaziridines of formula:

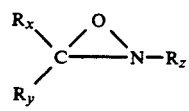

wherein:
R$_x$ is F, a perfluoroalkyl group having 1 to 10 carbon atoms or a —NR$_z'$ group in which R$_z'$ is a perfluoroalkyl group having 1 to 10 carbon atoms,
R$_y$ is F or a perfluoroalkyl group having 1 to 10 carbon atoms, and
R$_z$ is a perfluoroalkyl group having 1 to 10 carbon atoms, said process comprising reacting a perfluoro-imine of formula:

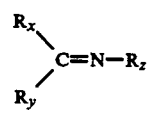

wherein R$_x$, R$_y$ and R$_z$ are the same as defined above, with an aromatic peroxyacid of formula:

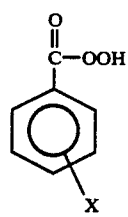

where X is selected from the group consisting of F, Cl, —NO$_2$, —COOR and —CONR$_2$, wherein R is H or an alkyl group having 1 to 5 carbon atoms, in an aprotic solvent, at a temperature ranging from −50° to +100° C.

2. The process of claim 1, wherein X is Cl and is in meta position with respect to the peroxycarboxylic group.

3. The process of claim 1, wherein R$_x$ and R$_y$ are F.

4. The process of claim 3, wherein R$_z$ is —CF$_3$.

5. The process of claim 1, wherein the solvent is selected from nitriles, ethers and chlorinated hydrocarbons or mixtures thereof.

6. The process of claim 5, wherein the solvent is selected from the group consisting of acetonitrile, benzonitrile, diethylether, dioxane, tetrahydrofuran, 2-methoxyethylether, dichloromethane, tetrachloromethane, chloroform, mono-chloroethane, and mixtures thereof.

7. The process of claim 6, wherein the solvent is dichloromethane.

8. The process of claim 6, wherein the solvent is acetonitrile.

* * * * *